United States Patent [19]

Kemper et al.

[11] Patent Number: 5,438,996
[45] Date of Patent: Aug. 8, 1995

[54] AMBULATORY, ULTRASONIC TRANSIT TIME, REAL-TIME, CERVICAL EFFACEMENT AND DILATATION MONITOR WITH DISPOSABLE PROBES

[75] Inventors: W. Scott Kemper, San Diego; Michael P. Guberek, Encinitas, both of Calif.

[73] Assignee: Triton Technology, Inc., San Diego, Calif.

[21] Appl. No.: 322,613

[22] Filed: Oct. 12, 1994

[51] Int. Cl.$^6$ .................................. A61B 8/00
[52] U.S. Cl. ....................... 128/661.02; 128/775; 128/778
[58] Field of Search .............. 128/660.01, 660.02, 128/660.06, 661.02, 662.03, 662.06, 675, 774, 775, 778

[56] References Cited

U.S. PATENT DOCUMENTS

| | | | |
|---|---|---|---|
| 4,349,033 | 9/1982 | Eden | 128/774 |
| 4,873,986 | 10/1989 | Wallace | 128/775 |
| 5,265,612 | 11/1993 | Sarvazyan et al. | 128/662.06 |

Primary Examiner—George Manuel
Attorney, Agent, or Firm—William C. Fuess

[57] ABSTRACT

Preferred transducers in the substantial shapes of a three-dimensional bodies, normally spheres or cylinders, emit ultrasound omni-directionally. The transducers are secured to the wall of the cervix uteri of human female, preferably by a barb or corkscrew coil, so that a straight line ultrasonic acoustic path exists between them. An ultrasonic transit time sonomicrometer detecting a variable propagation delay between the transducers dependent upon the dilatation or effacement of the cervix uteri serves as a ultrasonic cervimeter. Cervical dimension, and changes in dimension, developed by the ultrasonic cervimeter directly in millimeters are (i) validated for reasonableness, (ii) monitored so as to generate several alarms upon the occurrence(s) of several predetermined conditions, (iii) displayed, and (iv) archived all in a battery-powered ambulatory instrument.

26 Claims, 8 Drawing Sheets

ADVANTAGES AND DISADVANTAGES OF CERVIMETRY METHODS

| | Digital Cervimetry | Mechanical Cervimetry | Magnetic Cervimetry | Previous Ultrasonic Cervimetry | Present Invention Cervimetry |
|---|---|---|---|---|---|
| Installation | Easy | Difficult | Difficult | Difficult | Difficult |
| Patient comfortable during installation | No | No | No | No | No |
| Patient comfortable after installation | Yes | No | Yes | Yes | Yes |
| Convenience | High | Low | Moderate | Moderate | High |
| Measurement by stretching | Yes | Yes | No | No | No |
| Possibility of digital pelvic examination | Yes | No | Diminished | Diminished | Slightly Diminished |
| Output stability | Subjective | Calipers moveable (1) | Relies on signal intensity (2) | Relies on signal transit time; good | Relies on signal transit time; good |
| Output linearity | Subjective | Yes, almost Yes (3) | Not always (5) | Yes | Yes |
| Recording up to full dilatation | Yes | No; limited (4) | No | Yes | Yes |
| Patient Ambulatory | No | No | No | No | Yes |
| Monitoring, with history | No | No | No | Limited | Total |
| Monitoring, with alarms | No | No | No | Yes | Yes |

Figure 1

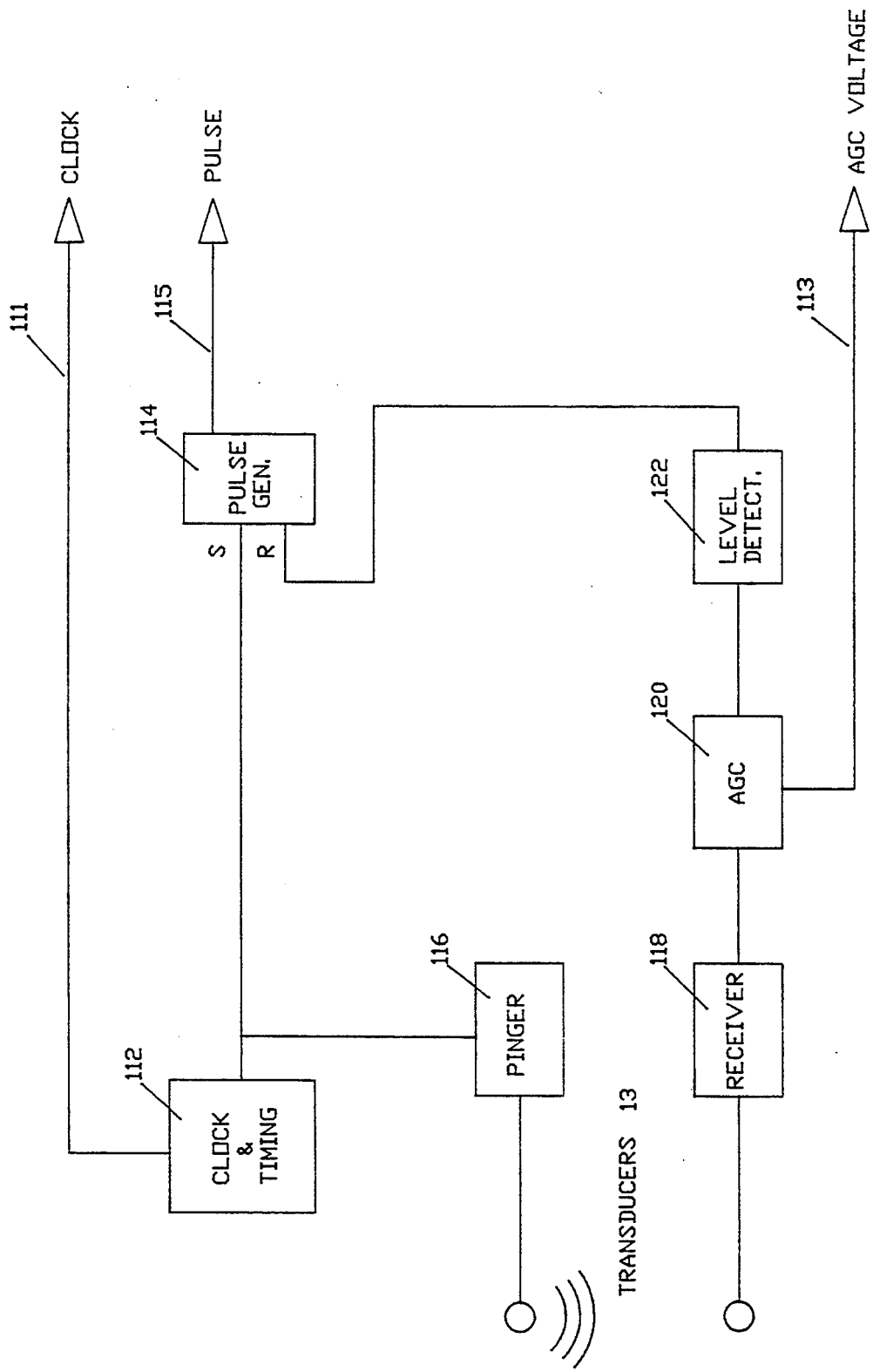

AMBULATORY, ULTRASONIC TRANSIT TIME, REAL-TIME, CERVICAL EFFACEMENT AND DILATATION MONITOR WITH DISPOSABLE PROBES

BACKGROUND OF THE INVENTION

1. Field of the Invention

The present invention generally concerns cervimetry and cervimeters, particularly such as use ultrasound as a basis of measurement.

The present invention particularly concerns real-time ultrasonic transit time cervimeters and cervical dilatation/effacement monitors, and probes usable with such cervimeters and/or cervical dilatation/effacement monitors.

2. Description of the Prior Art

Cause and constant supervision of high-risk pregnancies has historically involved the use of what were, at the times introduced, new and advanced technologies. This lengthy background has led, culminating in the present invention, to the continuous recording and monitoring of cervical dilatation during labor by means of ultrasonic cervimetry.

The ancients knew that the dilatation of the cervix, discernable with and by the fingers during manual digital assessment, attended the onset of labor in the human female.

2.1 The General History of Cervimeters Including Ultrasonic Cervimeters, and of the Measurements Obtainable With Such Cervimeters Current medical knowledge of cervical behavior descends largely from a huge base of historical data obtained by repeated digital palpation or 'digital cervimetry' during labor. Both vaginal and rectal examination have been used. The latter method was introduced by Kroenig to prevent ascending uterine infection. Reference Kroeig, A.. Der Ersatz der inneren Untersuchung Kriessender durch die Unteersuchung per Rectum; CENTRALBL GYNAKOL 1894; 18:235-243. Semmelweiss'classic work involving the relationship between vaginal examination and puerperal infection is well appreciated. Reference Semmelweiss, I., in Von Gorky, Y., ed., Semmelweiss gesammte Werke, Jena. 1905, VEB Gustav Fisher Verlag.

Although digital examination offers valuable clinical information on the progress of labor, its intermittent character does not allow an assessment of the dynamics of cervical dilatation. For that reason many attempts have been made to construct devices, cervimeters, for objective and continuous measurement of cervical dilatation based on (electro) mechanical, electronic and ultrasonic principles. A historical overview of some of nineteen various instruments published since the early fifties is presented in the article Assessment of cervical dilatation during labor; a review, by T. vand Dessel, et al. appearing in EUR. JNL. OBS. GYN. & REP. BIO. 41 (1991) 165–171.

Instrument-based cervimetry, or cervical dilatation measurement, has in particular been performed by mechanical, magnetic and/or ultrasonic means. A history of instrument-based cervimetry is presented by Moss, P. L., et al. as Continuous cervical dilatation monitoring by ultrasonic methods during labor, appearing in AM. J. OBSTET. GYNECOL. 132:16, 1978. The following text is derived from that article.

Moss, et al. point out that Friedman was the author in 1936 of a report discussing mechanical cervimetry. See Friedman, E. A.: Cervimetry, an objective method for study of cervical dilatation in labor, AM. J. OBSTET. GYNECOL. 71:1189, 1956. This paper was followed by another paper co-authored with Von Micsky in 1963. See Friedman, E. A., and Von Micsky, L. I.: Electronic cervimeter, A research instrument for the study of cervical dilatation in labor, AM. J. OBSTET. GYNECOL. 87: 789.

Siener cooperated with West from 1962 to 1972, and with Krementsoy in 1968, in the use the same method. See Siener, H.: An apparatus for recording the opening of the cervix during labor, ZENTALBL GYNAEWKOL 78: 2069, 1956; Siener, H.: A new electromechanical apparatus for measuring labor activities by the execution of combination measurements, ARCH. GYNAEKOL. 196: 365, 1961; Siener, H.: First stage of labor recorded by cervical tonometry, AM. J. OBSTET. GYNECOL. 86:303, 1963; Siener, H. and West, I.: Internal isometry and graphic registration of cervix dilatation as a basis for calculation of labor effectiveness and soft tissue resistance, GEBURTSHILFE FRAUENHEILKD 32: 123. 1972; and Krementsoy, U.: Improved technique for measurement of cervical dilatation, BIOMED. ENG. (N.Y.) 2: 350 1968.

The magnetic cervimeter was first proposed by Smith in 1954. See Smith, C. N.: Measurement of the forces and strains of labor and the action of certain oxytocic drugs, International Congress of Obstetrics and Gynecology, Geneva, 1954, S. A. George, P. 1030. However there were many drawbacks and it was only in 1971 that Rice, and also Kriewall, tried to solve these problems. Reference Rice, D.A.: Mechanism and measurement of cervical dilatation. Doctoral thesis, Purdue University, Lafayette, Indiana, 1974. Reference also Kriewall, T. J.: Measurement and analysis of cervical dilatation in human parturition, Doctoral theses, University of Michigan, Ann Arbor, Mich. 1974.

Ultrasonic cervimetry was introduced in the period from 1974 to 1976 by Neuman, Wolfson, and Zador. Reference Neuman, M. R. Wolfson, R. N. and Zador, I,: Ultrasonic transit time methods for monitoring the progress of obstetrical labor, TRANSACTIONS 0F PROFESSIONAL GROUP ON ULTRASONICS—IEEE, Vol. 33, 1975; Zador, J.: Ultrasonic determination of cervical dilatation during labor, Master's thesis, Case Western Reserve University, Cleveland, Ohio, 1974; Zador, I, Neuman, M. R. and Wolfson, R. N.: Continuous monitoring of cervical dilatation during labour by ultrasonic transit-time measurement, MED. BIOL. ENG. 14–229, 1976; and Wallenburg, H. C. S., and Wladimiroff, J. W.: Ultrasonic measurement of cervical dilatation during labor, AM. J. OBSTET. GYNECOL. 126:288, 1978.

A comparison of the advantages and inconveniences of each prior art method is shown in the first four columns of the Table of FIG. 1.

2.2 Ultrasonic Cervimetry

A typical advanced method of ultrasonic cervimetry, and the analysis of the measurements obtained thereby, was expounded by Moss, P. L., et al. in the aforementioned paper Continuous cervical dilatation monitoring by ultrasonic methods during labor, appearing in AM. J. OBSTET. GYNECOL. 132: 16, 1978.

The major goal of Moss, et al., as stated in their own words, was to evaluate ultrasonic cervimetry and to look at the characteristics of the recordings with respect to conventional variables of fetal monitoring. In particular, Moss, et al. looked at the relationship between dynamic changes in cervical dilatation and intrauterine pressure. They looked at both the amplitudes of the changes and the phase relationships between the two signals.

The installation of the transducers consisted of fixing two piezoelectric crystals, each of dimension 1 mm by 5 nun, to the external os of the uterine cervix. The installation took place at 3 cm or more of dilatation. The crystals were fixed in places dramatically opposed to each other and were so held in position by spring-loaded clips.

The ultrasonic cervimeter in use generated an ultrasound wave each second, and the total time elapsed from the emission of that signal by one crystal to the reception by the other was compiled and converted into a distance. The ultrasound wave velocity was considered to be constant at 1.48 mm per microsecond. Since time, and not intensity, of the signal was the important parameter, the crystals had to rotate more than 60° degrees from one another before an error in the measurements was introduced. Migration was not possible since the clips teeth, when closed, pierced the cervix through and through.

The dilatation value along with the fetal heart rates, the fetal electrocardiograms, and the uterine contractions were recorded on an eight channel recorder.

Clinical accuracy was 0.6 cm. When the ultrasound recording of cervical dilatation is compared to the intrauterine pressure curve, it is characterized by a baseline and wave-shape curve of dilatation (DWP). The maximal amplitude component is called cervical maximal plasticity. The onset of the DWP is related to cervical resistivity, and the end of DWP reflects the relaxation time of cervical dilatation. The data show that as dilatation enters the active phase of labor, the plasticity, the resistivity, and the duration Of relaxation of the cervix increase. These observations are related to the structural changes of the cervix during labor. (AM. J. OBSTET, GYNECOL. 132.16 1978).

It was noted by Moss, et al. (op. cit.) that cervical dilatation and fetal descent can be monitored simultaneously by ultrasound.

2.3 Problems with Previous Cervimeters—Mechanical and Electromechanical Cervimeters The analysis of this section 2.3, and of the following sections 2.4 and 2.5, is a substantial extract and paraphrase of the aforementioned article Assessment of cervical dilatation during labor: a review, by T. van Dessel, J. H. M. Frijns, F.Th.J.G.Th. Kok, and H. C. S. Wallenburg appearing in EUROPEAN JOURNAL OF OBSTETRICS & GYNECOLOGY AND REPRODUCTIVE BIOLOGY, 41 (1991) 165–171.

Two main prototypes of mechanical cervimeters have been described, the calipers-type and the string-type.

In the basic calipers-type cervimeter, X-cross calipers equipped with a centimeter rule at the distal end are used to measure the distance between opposing cervical rims. The Krementsov cervimeter, called an 'orificiometer' [18], has a ring at each proximal caliper end in which the fingers of the examiner can be placed. See Krememtsov, Y. G., Improved technique for measurement of cervical dilatation, BIOMED. ENGIN. 1968:2:350. It enables the examiner to verify his findings by vaginal examination. The Tervila cervimeter consists of two pairs of Kelly clamps, attached separately to the cervical edges, and connected in a hinge-like way. See Tervila, L. , Measurement of cervical dilatation in labour, AM. J. OBSTET. GYNECOL. 1953; 51:374–376. The Friedman cervimeter is equipped with bulldog clips for attachment to the cervical rims. See Friedman, E. A., Cervimetry: an Objective method for the study of cervical dilatation in labor, AM. J. OBSTET. GYNECOL. 1956; 71:1189–1193. Measurement is continuous, but readings are obtained at 2 to 10 minute intervals and plotted manually against time.

Disadvantages of these simple mechanical cervimeters are the discontinuity of readings, the lack of recording facilities and the quite heavy mechanical construction that interferes with dilatation during measurement.

In later years, low-weight calipers with cervical attachment clips were combined with potentiometers to convert the movements of the caliper arms into an electrical signal that could be recorded on a polygraph. Electromechanical cervimeters of this basic type were described by Vossius, G. in Fine Methode zur quantitativen Messung der Erweiterung und des Tiefertretens des Muttermundes Wahrend der Geburt. Z GESAMTE EXP MED 1961; 134:506–512, by Svoboda, M. in CSL. GYNAEKOL 1958; 23:621–623, cited by Warm R., Ueber die Messung der Muttermundseroffnung unter der Geburt. Z Arztl Fortbild 1967; 61:661–666, by Richardson, J. Aa, Sutherland, I. A., Allen D. W., and Dore F., in The development of an instrument for monitoring dilatation of the cervix during labour; BIOMED. ENGIN. 1976; 11: 311313, and by Richardson JA, Sutherland IA;. Measurement of cervical dilatation during labour; Physical science techniques in obstetrics and gynecology, Tunbridge Wells: Pitman Medical, Kent, United Kingdom, 1977. In the paper The electromechanical Friedman cervimeter by Friedman, EA, and Von Micsky, LI, an electronic cervimeter is taught as a research instrument for the study of cervical dilatation in labor. Reference AM. J. OBSTET. GYNECOL. 1963; 87:789–792. The Freidman electronic cervimeter is attached to the cervix by a retractable row of needles. At a preset dilatation the needle attachments to the cervix are automatically released. In another instrument developed and expounded by Langreder, W. in Geburtshilfliche Messungen, BIBL. GYNAECOL 1965; 20 (S), movements are recorded by means of a photoelectric cell. The cervimeters described by Warm, R. in Ueber die Messung der Muttermundseroffnung unter der Geburt. appearing in Z. ARTZL FORTBILD 1967; 61:661–666, and by Kazda S. Brotanek V. in Part played by cervix in uterine activity at the onset of labour appearing in CSL. GYNAEKOL 1962; 27:333–337, have a similar design. A pair of calipers is connected to an invisible hinge in a heavy extravaginal part containing an internal potentiometer. Kazda and Brotanek report successful recordings in 90 patients without presenting data.

Siener has reported several cervimeters. The original Siener cervimeter was reported by Siener H., Ein neues elektromechanisches Wehenmessgerat zur Durchfuhrung yon Kombinationsmessungen, ARCH. GYNAKOL 1961; 196; 365–372, by Siener H., First stage of labor recorded by cervical tonometry; AM. J. OBSTET. GYNECOL. 1963; 86: 303309, by Siener H. and Wust L. Innere Wehenmessung und graphische Registrierung der Muttermunds-Eroffnung als Grundlagen zur Berechnung der Weheneffektivitat und des Weichteil-widerstandes; GEBURTSH FRAUENHEILK 1972; 32:125–130. It was also reported by Embrey M. P. and Siener, H. Cervical tocodynamometry; J. OBSTET. GYNAECOL. BRIT. COMMONW. 1965; 72:225–228, and in Siener H., Cervical dynamometry, a new method in obstetrical research; AM. J. OBSTET. GYNECOL. 1964; 89:579–582. The Siener cervimeter offers the opportunity for both measurement of cervical dilatation and measurement of cervical dilatation forces, after fixation of the calipers. Later Siener used the concept of the electromechanical calipers cervimeter to construct even more sophisticated devices: the cervical dynamometer and the 'erweiterte Zervixwehenmesser' ('expanded cervix-contraction meter'). Reference Siener H., Die erweiterte Zervixwehenmessung; GEBURTSH FRAUENHEILK 1959; 19:140–145. The cervical dynamometer allowed measurement of the pressure of the fetal head on the cervix after fixation of the intravaginal arms of the cervimeter. The 'expanded cervix-contraction meter' combined a calipers cervimeter with a metal construction for measurement of fetal descent.

The string-type cervimeter consists of strings or cords, attached to the cervix. Changes in dilatation cause changes in length of the strings which are transmitted to a kymograph by a mechanical pulley-guided system. Reference Siener H., Studien uber das Verbalten des Muttermundes wahrend der Eroffnungsperiode; ARCH. GYNAEKOL 1957; 118:556–576. Alternatively, the changes could be electrically communicated by a linear differential transformer. Reference Smyth C. N., Measurement of the forces and strains of labour and the action of certain oxytocic drugs. Comptes Rendus du Congres International de Gynecologie et d'Obstetrique, Geneva, 1954; 1030–1039.

Some instruments are described for assessment of cervical properties other than dilatation. Glass and co-workers has used the medical engineering principle of indentation to design an electromechanical device for measurement of, the relative softness of the cervix. Reference Glass BL, Munger RE, Johnson WL; Instrument to measure tissue softness of the uterine cervix in pregnancy; MED. RES. ENGIN. 1968; 7:34–35. An instrument to measure the amount of pressure of the fetal head on the cervix has been reported by Noack and Blaschkowski. Reference Noack H. and Blaschkowski E., Zur Frage der graphischen Registrierung von Kontraktionen des Muttermundes unter der Geburt; Z. GYNAKOL 1958; 80:1609–1616.

Mechanical cervimeters are cumbersome in clinical practice and they cannot be used for continuous measurement of dilatation. Most electromechanical devices offer the possibility of continuous registration but have the disadvantage of a mechanical intravaginal part, which may interfere with cervical dilatation.

2.4 Problems with Previous Cervimeters—Electromagnetic Cervimeters

Electromagnetic cervimeters were described by Wolf in a his congress report: Wolf W., Kongressbericht. ARCH. GYNAKOLOGIE 1951; 180:177–180; and later by Rice, D. A. in Mechanism and measurement of cervical dilatation; Doctoral dissertation. 1974, Purdue University, Lafayette, Ind. U.S.A. With these cervimeters cervical dilatation is measured using two small induction coils, attached to opposing cervical rims. An electrical current, sent through one of the coils, establishes a magnetic field that is detected in the opposite coil and then recorded. Kriewall has used a permanent magnet dipole as a magnetic field source and two Hall-effect magnetic-field transducers as detectors. Reference Kriewall, T. J., Measurement and analysis of cervical dilatation in human parturition; Doctoral thesis, 1974, University of Michigan, Ann Arbor, Mich., U.S.A. The signals derived with this technique are processed to determine the distance between the transducers.

Electromagnetic cervimeters with clinical applicability have not been described.

2.5 Problems with Previous Cervimeters—Ultrasound Cervimeters

Abdominal routes have been used to visualize cervical dilatation by means of ultrasound during pregnancy. Reference Sarti D. A., et al. Ultrasonic visualization of a dilated cervix during pregnancy; RADIOL. 1979; 130:417–420; Varma T. R., Patel R. H., and Pillai U. Ultrasonic assessment of cervix in normal pregnancy; ACTA. OBSTET. GYNECOL. SCAND. 1986; 65:229–233; Parulekar S. G. and Kiwi R., Dynamic incompetent cervix uteri; J. ULTRASOUND MED. 1988; 7:481–485

Vaginal routes have been used to visualize cervical dilatation by means of ultrasound during pregnancy. Reference Balde M. D., Stolz W., Unteregger B., and Bastert G.; L'echographic transvaginale, un rapport dans le diagnotic de la beance du col uterin; J. GYNECOL. OBSTET. BIOL. REPROD. (Paris) 1988; 17:629–633

Transperineal routes have been used to visualize cervical dilatation by means of ultrasound during pregnancy. Reference Lewin B., L'echotomographie perineale. Une nouvelle methode de mesure objective du col; J. GYNECOL. OBSTET. REPROD. 1976; 5:289–295; and Jeanty P., Perineal scanning; AM. J. PERINATOL. 1986; 3:289–95

Reports in the literature dealing with systematic visual assessment of cervical dilatation during labor could not be found by T. van Dessel, et al. (op. cit.), nor by Applicants.

A different approach uses two ultrasound transducers attached to opposing rims of the cervix. An ultrasonic signal generated by one transducer is received by the opposing one. Since the ultrasound velocity is known, the transmission time allows computation of the distance between the transducers.

The first ultrasound cervimeter was described by Zador et al. in 1974. Reference Zador, I, Neuman, M. R., and Wolfson, R. N.; Continuous monitoring of cervical dilatation during labour by ultrasonic transmittime measurement; MED. BIOL. ENGIN. 1976; 14:299–305; also Zador, I, Wolfson R. N., and Neuman, M. R., Ultrasonic measurement of cervical dilatation during labor; ANN. CONF. ENGIN. MED. BIOL. 1974; 16:187. These authors used spring-loaded clips to attach the transducers to the cervix. A total of 24 readings of women in labor were reported, but no specific data were given. Apparently, practical problems were encountered, because further clinical studies with this device could not be found.

A similar cervimeter has been presented by Kok et al. in 1976 in preliminary reports. Reference Kok, F. T., Wallenburg, H. C., and Wladimiroff, J. W., Ultrasonic measurement of cervical dilatation during labor; AM. J. OBSTET. GYNECOL. 1976; 126:288–290; also Eijskoot, F., Storm, J., Kok, F. T., Wallenburg, H., and Wladimiroff, J.; An ultrasonic device for continuous measurement of cervical dilatation during labor; ULTRASONICS 1977; 55:183-185. The problems with the fixation of the transducers to the cervix were eliminated by using special spiral-shaped transducers. The data was analyzed off-line by a computer, and accuracy and precision in vitro and in vivo were shown to be good in a well-documented study of 62 women in labor. Reference Kok, FTJGT; Ultrasonic cervimetry (summary in English); PhD-Thesis, Erasmus University, School of Medicine and Health Sciences, Rotterdam, 1977.

Cervical dilatation appeared to follow a wave pattern reflecting the intrauterine pressure curve. Maximal cervical dilatation coincided with the maximal intensity of each contraction. Generally, the derived curve of cervical dilatation showed the sigmoid shape postulated by Friedman (op. cit.) and by Krementsov Y. G. in Improved technique for measurement of cervical dilatation; BIOMED. ENGIN. 1968; 2:350. A decelerative phrase was never detected. Using a similar device Moss and coworkers have investigated 13 women in labor. Reference Moss PL, Lauron P., Roux JF, Neuman MR, and Dmytrus KC; Continuous cervical dilatation monitoring by ultrasonic methods during labor;AM. J. OBSTET. GYNECOL. 1978; 132:16-19. T. Van Dessel, et al. (op. cit.) observed—contrary to the findings reported by Kok, Zador I, Neuman MR, Wolfson RN in Continuous monitoring of cervical dilatation during labour by ultrasonic transmit-time measurement. MED. BIOL. ENGIN. 1976; 14:299-305—that the peaks of uterine contraction and cervical dilatation were out of phase.

Ultrasound visualization of the cervix may be helpful in monitoring the patient at risk for premature delivery, but does not allow continuous registration of dilatation during labor. However, ultrasonic cervimetry does offer continuous and reliable recording with little discomfort to the patient, but clinical data has been limited. T. van Dessel, et al., (op. cit.) felt in 1991 that "[u]ltrasound cervimetry may be a useful research tool for the study of the cervical response to the uterine contractions during labor. For clinical obstetric purposes, however, digital assessment of cervical dilatation seems sufficient."

2.6 The Desirability of Continuous Accurate Convenient Cervical

Dilation/effacement Monitoring, with Automated Alarms

The inventors of the present invention are of a contrary opinion to the opinion of T. van Dessel, et al., (op. cit.) in the aforementioned paper that "digital assessment of cervical dilatation... [is] sufficient" and that, by implication, ultrasound cervimetry has no role in the clinical environment.

In the first place, the only realistic alternative to ultrasonic cervimetry is, and has proven to be, no cervimetry at all, and exclusive reliance the time-honored approach of digital assessment of cervical dilatation. This procedure, which should be, and regularly is, performed every hour after the onset of labor, is (i) manifestly inadequate to detect the onset of labor itself, (ii) laborious, (iii) without automatic contemporaneous generation of a permanent record, and (iv) of no greater quality in results obtained than the skill and attentiveness of the practitioner.

Despite the lack of clinical, or patient portable, instrumentation for the detection of the onset of labor (should such event be sharply definable, and it is), the detection of this event is very important in those rare cases where premature labor must be avoided. The inventors of the present invention are involved in the verification of instrument with one of the major centers for the management of problem pregnancies and premature births in the United States if not also the world circa 1994. Prolongation of gestation beyond a certain, threshold, number of weeks is currently very, even crucially, important to the survival of the fetus at birth. This minimum gestation period for live birth has greatly decreased in recent years, but cannot be expected to decrease to shorter than the period within which spontaneous abortions, or premature labor, occur in the human female. Accordingly, the only way that some fetuses will ultimately be viable is if tenure in the womb is prolonged.

Powerful drugs exist to arrest labor. However, these drugs cannot be continuously, or even regularly administered, during the projected terminal phase (at whatsoever period gestation) of a particular problem pregnancy. Accordingly, it is of crucial importance to detect the onset of labor (should such event be detectable, and it is) at the earliest possible moment in order that it may be stopped, if desired or required, by the administration of drugs or otherwise.

Next, once labor has begun, and even in normal pregnancies and deliveries, the inventors of the present invention do not take such a cavalier attitude as do their peers to the present lack of hard, recorded, and/or instantaneous quantitative data about what has gone on, and is going on, from moment to moment during labor. The dilatation/effacement of the cervix is a very good indicator of the progress, and or of problems, with labor.

2.6.1 Timing of Therapeutic Regimens Based in Cervical Dilation/Effacement Monitoring The first, and potentially greatest, advantage to the continuous monitoring of cervical dilatation/effacement during labor, if not also in the period before, is that it can promote superior timing in the administration of medical therapies to support the suppression of labor or during labor. Cervical dilatation/effacement monitoring promotes the timely and optimally timed therapeutic administrations in consideration of (i) the earliest possibly recognition of changing conditions, including problem conditions, during labor, (ii) a definitive record of exactly how long certain conditions have persisted, and (iii) the possibility of machine aids, ranging from alarms to the comparison of profiles to mathematical modeling.

In short, the fact that most births occur normally even should the midwife or obstetrician be ignorant of cervical dilatation, and the complementary fact that some births encounter problems, are both facts of nature, and not of man. However, the fact that intervention in the birth process, primarily by Caesarian section, is occasionally ancient and generally successful does not invariably mean that it has been optimally timed for the health of the fetus and/or the mother.

Timing in the administration of therapeutic regimens during labor has always been recognized to be an issue. For example, the administration of pain-killing drugs to the mother is permissible during the early stages of labor whereas the administration of the same drugs becomes impermissible in later stages of labor. For example, a Caesarian delivery is not normally attempted until some lapse of reasonable progress towards a normal, vaginal, delivery. The questions that should be asked by a clinical practitioner in considering the efficacy of a monitor device in accordance with the present invention are these: Is there any evidence that the timing of some (or any) interventions is more critical than the timing of other interventions, or more critical than is generally recognized, or, God forbid, more critical that is generally possible under current methods for the measurement of the progress of labor? If so, what interventions would so benefit? Finally, is the monitoring of cervical dilatation and/or effacement (the thinning of the cervical rim, which thinning is of course proportional to the expansion of the cervix) an appropriate, or useful, measure of the progress, and/or the onset of problems, during labor? The present specification does not contain proof that the answers to the first and the third questions are yes, nor need it do so. However, such data from clinical trials as is still under development circa Apr. 1994 suggests that this "yes" answer.

The present invention does not concern the medical diagnosis of problems during delivery, which is part of the evolving medical art of obstetrics. The present invention does concern, however, new machines and methods for the comprehensive measurement and display of, and the generation of alarms from, cervical dilatation/effacement during labor.

2.6.2 The Communication of the History of a Birth Based in

Cervical Dilation/Effacement Monitoring

The oral record and the written does not suffice for the communication of the stages, and circumstances, of complicated labor. The hard-copy, graphical, record of a continuous monitoring of cervical dilatation/effacement during labor can promote a number of ends. It permits the ready visualization of the progress of the labor. It permits all temporal junctures at which therapies were administered to be identified, and the results of these therapies (insofar as affecting cervical dilatation/effacement) recognized. It permits the ready communication of a history of the labor to (i) students, (ii) history, (iii) medical review boards and courts, and (iv) other physicians, including those who may attend other labors of the same female some years hence.

2.6.3 Diligence in Childbirth Monitoring Based in the Monitoring of Cervical Dilation/Effacement Childbirth in humans is a lengthy process which can commence totally asynchronously with the other duties and schedule of an attending obstetrician or midwife. The attentiveness of personnel attending to the labor can sometimes languish over the long periods involved. It is equally as undesirable that these personnel should be overly zealous. It is (i) difficult, (ii) unreasonable on the basis of medical results obtained, (iii) and more disturbing than beneficial to the patient, that a physician or attending midwife should be making excessively frequent manual digital assessment of the dilatation of the cervix during labor.

Accordingly, manual assessment of cervical dilatation during labor that is either too infrequent, or too frequent, is avoided. However, there is a fair amount going on in the cervical dilatation on a time scale that is short, and thus insufficiently captured, relative to even the most frequent manual digital assessment. Namely, this dilatation is cyclic on a time scale of typically from one (1) to two (2) minutes, as will be shown in this specification. Moreover, there is no desire to delay the recognition of changes, especially such changes as may be significant, simply because they do not coincide with the periodic, and likely infrequent, schedule of manual digital assessment.

In most labors and deliveries, including those that have problems, observational vagaries as may result in (i) imprecision and/or (ii) untimeliness in detection/measurement of the dilatation/effacement of the cervix the are of no consequence. The challenge is with those few difficult, often premature, labors and deliveries in which the timeliness and quality of information may be, or become, critical. In episodes of labor of this sort the physician faces a dilemma. His continuing observational interventions may precipitate the very events that he/she seeks to avoid. Conversely, optimal intervention may be compromised if the physician is not in possession of the most timely and accurate information.

Accordingly, a system that would continuously, accurately and reliably monitor cervical dilatation/effacement during labor without substantial discomfort, inconvenience, disturbance or hazard to the patient would be very desirable. The present invention concerns such a system.

SUMMARY OF THE INVENTION

The present invention contemplates (i) a probe for an ultrasonic transit time cervimeter; (ii) an ultrasonic transit time cervimeter for quantitatively measuring the effacement, or dilatation, of the cervix uteri; (iii) a monitor of the effacement, or dilatation, of the cervix uteri; (iv) a real-time ambulatory recording and alarming monitor of the effacement, or dilatation, of the cervix uteri; and (v) methods of probe placement and automated cervical dilatation monitoring for the detection and alarming of the onset of labor, the progress of labor, and any problems developing during labor.

1. An Ultrasonic Transit Time Cervimeter Probe

A preferred configuration of an ultrasonic transit time cervimeter probe in accordance with the present invention consists of transducers in the substantial shapes of a three-dimensional, non-planar, bodies. Each such transducer body is characterized in that ultrasound emissions from the transducer occur along a multiplicity of axis in multiple different directions. The transducer body is, for example, in the shape of a sphere or, preferably, a cylinder.

When secured to the wall of the cervix uteri of human female, such as by a barbed fishhook or corkscrew coil, the transducers are substantially insensitive to their initial placement(s) and alignment(s), and also to any directional changes occurring before or during labor, serving to maintain good acoustic coupling under all conditions.

2. An Ultrasonic Transit Time Cervimeter

An ultrasonic transit time cervimeter in accordance with the present invention includes (i) an ultrasonic transmitter in the substantial shape of a three-dimensional, non-planar, body, and (ii) an ultrasonic receiver in the substantial shape of a three-dimensional, non-planar, body, and (iii) an ultrasonic transit time micrometer.

Both the transmitter and the receiver are characterized in that ultrasound emissions from the transmitter, or ultrasound reception at the receiver, may permissively transpire along a multiplicity of axis in multiple different directions. The ultrasonic transmitter, and also the ultrasonic receiver, are secured to the wall of the cervix uteri of human female at spaced apart positions so that a straight line ultrasonic acoustic path exists between them.

The ultrasonic transit time micrometer detects a delay in the propagation of ultrasound from the ultrasonic transmitter to the ultrasonic receiver. This delay, which changes with the dilatation or effacement of the cervix uteri, serves as an indication of the dilatation of the cervix uteri The ultrasonic transit time micrometer preferably makes (i) a first alarm upon such times as the detected ultrasound delay varies sufficiently (normally 10%), and sufficiently regularly over time (normally over an interval of 1-2 minutes, depending upon the type of mammal), so as to indicate a corresponding temporally regular cyclical variation in the dilatation of the cervix uteri. After actuating this first alarm, the ultrasonic transit time micrometer preferably makes (ii) another, second, alarm, upon any later time(s) that the detected ultrasound delay exhibits such an insufficient variation (less than 10%) over such an interval of time (normally over a period of greater than ten minutes) so as to indicate that the dilatation, or effacement, of the cervix uteri is no longer incurring a regular, cyclic, variation. The (i) first alarm, arising from temporally regular, cyclical, variations in cervix dilatation, generally indicates the onset of labor. Thereafter any (ii) prolonged cessation of this cyclical variation generally indicates the onset of problems with labor.

Still another alarm preferably sounds upon such times as the detected ultrasound delay is sufficiently great so as to indicate that the corresponding dilatation of the cervix uteri has exceeded a predetermined size.

3. An Ultrasonic Transit Time Cervical Dilatation Monitor

A complete automated ultrasonic transit time cervical dilatation monitor includes (i) an ultrasonic transmitter, (ii) an ultrasonic receiver, (iii) a mechanism securing the ultrasonic transmitter, and also the ultrasonic receiver, to the wall of the cervix uteri of human female at spaced apart positions so that a straight line ultrasonic acoustic path exists between the ultrasonic transmitter and the ultrasonic receiver, (iv) an ultrasonic transit time micrometer, connected to both the ultrasonic transmitter and the ultrasonic receiver in their positions secured to the wall of the cervix, for detecting a delay in the propagation of ultrasound from the ultrasonic transmitter to the ultrasonic receiver as an indication of the dilatation of the cervix uteri, and (v) a monitor of the indicated dilatation of the cervix uteri for making an alarm if a predetermined condition of cervical dilatation is detected.

One predetermined condition of the cervix that is monitored is any cyclical variations in cervical dilatation, an alarm being made upon the detection of such cyclical temporal variations in cervical dilatation as commonly indicate the onset of labor.

Another predetermined condition of the cervix that is monitored is the cessation of any cyclical variations in cervical dilatation once such variations have begun. An alarm is made upon the cessation of cyclical temporal variations after labor has once begun because any such cessation at this time commonly indicates the onset of problems with labor.

Still another predetermined condition of the cervix that is monitored is the indicated physical dilatation of the cervix. An alarm is made if this dilatation exceeds a predetermined distance.

A complete history of the periodic measurements transpiring during a predetermined period, normally one day, is stored in digital electronic form. In order to make this history more meaningful, local maxima and minima occurring during the period are recognized and stored, and not simply the measurements taken at arbitrarily predetermined time intervals.

The instantaneously measured dilatation/effacement of the cervix, and the (generally) cyclical trends in this measurement after the onset of labor may be associated with, an correlated with, the pressure on the uterus and the fetal head as is generally detected by another instrument in the form of a pressure sensor. In rare instances a digital electronic signal output normally available from the ultrasonic transit time micrometer of the ultrasonic transit time cervimeter of the present invention is compared, normally in a signal-monitoring and signal-displaying digital personal computer running signal processing software, with a like signal output from the pressure sensor instrument. (Even more rarely the two instruments may be combined, and portable.)

4 A Real-time Ambulatory Recording and Alarming Monitor of the Effacement, or Dilatation, of the Cervix Uteri A real-time, ambulatory, recording and alarming monitor of the effacement, or dilatation, of the cervix uteri in accordance with the present invention includes an ultrasonic transmitter, an ultrasonic receiver, and mechanism for securing the ultrasonic transmitter and the ultrasonic receiver to the wall of the cervix uteri of human female. The ultrasonic transmitter and receiver are located at spaced apart positions so that a straight line ultrasonic acoustic path at least partially within the cervix exists between them.

Additionally, and further, a case suitable for attachment to the body, normally by a belt at the waist, contains all necessary components of a real-time cervical effacement, or dilatation, monitor and alarm. An ultrasonic transit time micrometer is electrically connected to both the ultrasonic transmitter and the ultrasonic receiver in their positions secured to the wall of the cervix. The ultrasonic micrometer serves to detect a delay in the propagation of ultrasound from the ultrasonic transmitter to the ultrasonic receiver. This delay indicates the dilatation of the cervix uteri, or, depending upon the placement of the ultrasonic transmitter and receiver, and indication of the effacement (thinning) of the cervix.

A memory within the case stores a history of the delays as are detected over time as an indication of the an pattern, or cyclical pattern, of the dilatation (or effacement) of the cervix uteri.

A display within the case displays at times, and from time to time, each of (i) the present, instantaneous, dilatation (effacement) of the cervix uteri, and also (ii) a representation of the dilatation (effacement) of the cervix uteri over a time interval ending at present.

An alarm circuit within the case causes an alarm if the indicated dilatation (effacement) of the cervix uteri equals a predetermined condition, or if the history of the dilatation (effacement) of the cervix uteri falls within the parameters of a predetermined model. The predetermined conditions that are continuously repetitively monitored for producing an alarm are (i) the onset of any such cyclical periodic dimensional changes of the cervix as mark the onset of labor, and/or (ii) any dilatation of the cervix to a certain size. Once labor with its attendant cyclic variations in the dilatation of the cervix has begun, (iii) any cessation in the cyclic variations of the dilatation of the cervix is thereafter monitored, with an alarm being produced if these variations fall outside the range of a predetermined model.

5. Probe Placement for An Ultrasonic Transit Time Cervimeter, or Cervical Dilatation Monitor Both the cervimeter, and the automated cervical dilatation monitor, of the present invention are preferrably used with a probe consisting of at least two transducers. These transducers may be conventionally secured to the wall of the cervix on opposite ends of major chord, or diameter, of the circular cervix. The transducers need not be so placed, however.

The transducers can be disposed along a minor chord (the segment of a secant between its intersections with the curved wall of the cervix). As this minor chord varies in length, so does the diameter, and the dilatation, of the entire cervix.

The transducers can even be disposed at spaced-apart positions between a first point upon an interior wall of the cervix uteri and a second point radially disposed to the exterior of the first point along an extension of a vector between an imaginary central axis of the cervix uteri and the first point. This path varies in length as the wall of the cervix uteri changes from thick to thin, which changes are directly related to the increase in diameter, or dilatation, of the cervix.

It is accordingly not necessary that the ultrasonic transducers should be located directly opposite from each other across the diameter of the circular cervix.

These and other aspects and attributes of the present invention will become increasingly clear upon reference to the following drawings and accompanying specification.

BRIEF DESCRIPTION OF THE DRAWINGS

FIG. 1 contains a table comparing the advantages and inconveniences of prior art methods of cervimetry with the method, and instrument, of the present invention.

FIG. 6 is a schematic block diagram of a substantially analog first portion of the preferred embodiment of the ambulatory cervical effacement/dilatation monitor in accordance with the present invention previously seen in FIG. 2.

DESCRIPTION OF THE PREFERRED EMBODIMENT

Figure 2:
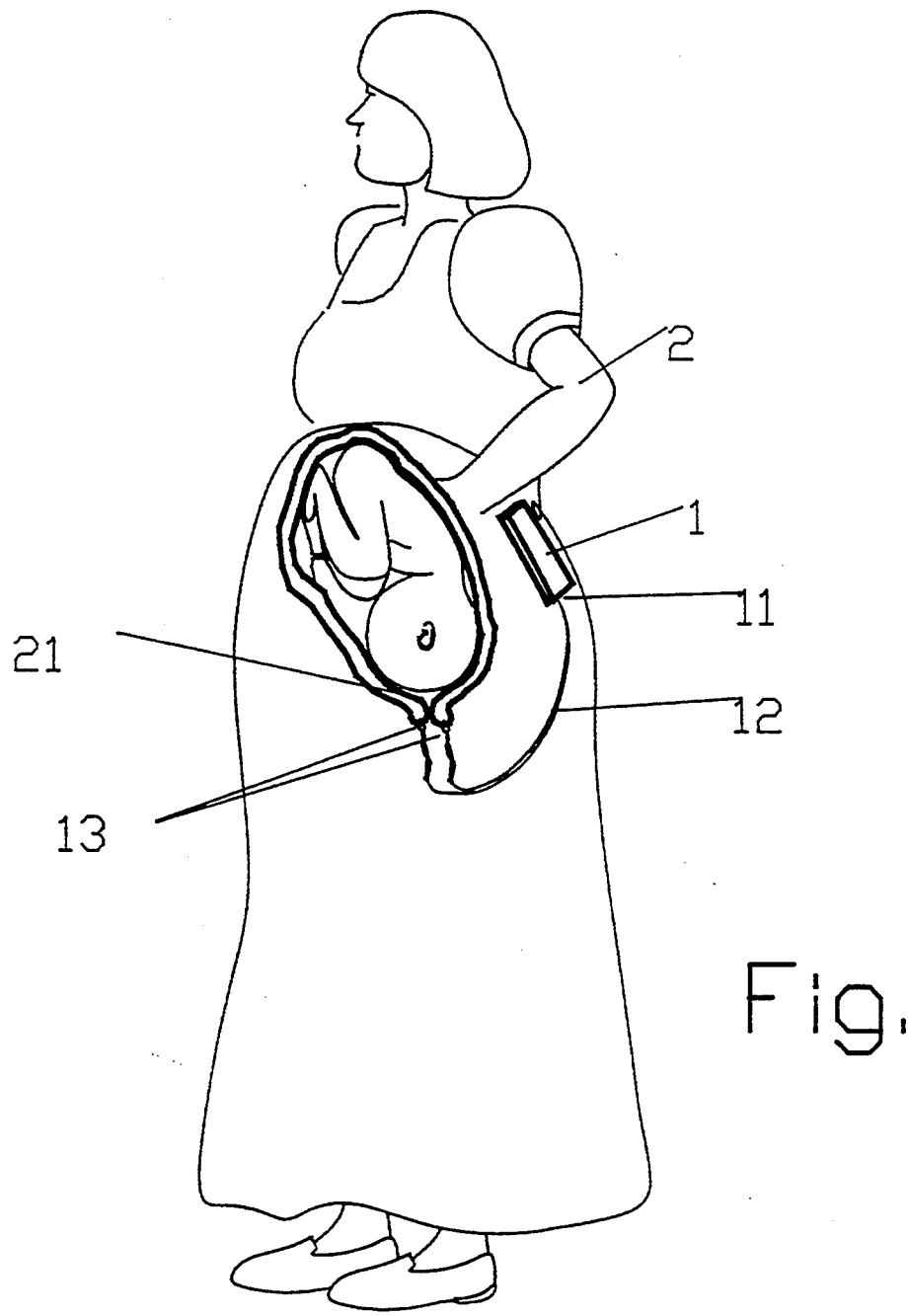
FIG. 2 is a diagrammatic perspective view showing a preferred embodiment of an ambulatory cervical effacement/dilatation monitor having disposable probes in accordance with the present invention in use for monitoring an ambulatory pregnant human female.

The present invention is directed to measuring and to monitoring the dilatation—meaning opening—or, equivalently, the effacement—meaning the thickness of the rim—of the cervix uteri, particularly the cervix uteri of a human female particularly during labor. It should be noted that as the cervix expands during labor, increasing the dilatation distance, the rim of the cervix stretches and becomes thinner, decreasing the effacement distance, or thickness of the rim. One phenomena is related to the other. Both phenomena show the same cyclical variation during labor, and each may be correlated to the other.

The probes of an ultrasonic acoustic cervimeter in accordance with the present invention are preferrably affixed across the major chord, or diameter, of the cervix uteri from a one side to the other, or at least across a minor chord for such a maximum distance of separation on the face of the cervix as is possible. In such positions the probes measure dilatation.

However, the probes may be affixed, if required or desired, along but a single radii of the cervix with a one probe located more centrally, on an interior wall of the cervix (which is in the overall shape of a torus) and with the remaining probe located nearby on the exterior wall of the cervix. In such a position the probes measure effacement.

An instrument in accordance with the present invention may be implemented in many different forms—ranging from a straightforward ultrasonic acoustic distance measuring device, or sonic cervimeter, to a full-blown computerized cervical dilatation/effacement alarming monitor with a memory and a time-based display of a running history of dilatation/effacement measurements. One preferred, basic, embodiment is as a battery-powered monitor with a memory and a graphical display, plus combined audible and visual alarm indications, that is completely self-contained and portable, and that is intended for continuous use on, partially within, and by, an ambulatory female patient. This embodiment will typically take one hundred (100) measurements a second, forming a running average of the cumulative measurements taken over a period of five (5) seconds and displaying the averaged measurements for the previous one hundred and twenty-eight (128) five-second intervals (for a total of 10⅔ minutes). The cumulative measurements for a longer period are stored to the capacity of memory, typically the averaged measurements for at least the previous six hundred and forty (640) five-second intervals for a total of over sixty (60) minutes). The ambulatory monitor typically so functions on two (2) 9 v.d.c. dry cell batteries, typically for a period of more than eight weeks.

A table comparing the major advantages and inconveniences of prior art methods of cervimetry with the method, and instrument, of the present invention is shown in FIG. 1. It may immediately be observed that the ultrasonic cervimetry method of the present invention serves, nonetheless to being performed by an instrument that is uniquely compact and suitable for ambulatory use, to record a history of cervical dilatation-/effacement that is described as "total" as opposed to "limited". By this it is meant that previous monitors, especially including ultrasound monitors, recorded a history of cervical dilatation/effacement only when the patient was "hooked up" to the previous monitors, usually in a hospital after the onset of labor. Data regarding any such long or short term transient events during pregnancy as did not lead to the full onset of labor was unrecorded and unavailable. Indeed, very little is known at the present time about exactly what (other than the lapse of time, or intentionally-administered medications) will most likely induce the onset of labor in a particular human female, and what precursors to this event and/or flags to the likely causative agent(s) (such as exercise, or diet, or temperature) might be observed. The cervical monitor of the present invention is, of course, dedicated to providing a full and complete record of cervical dilatation/effacement over a period potentially as long as many months. During this period of time there is little or nothing regarding the dilatation (or, equivalently, the effacement) of the cervix that will not be recorded, and archived into a history store that is retrievable to and analyzable by, a health care professional. Accordingly, the recorded history is described as "total".

Because the cervical monitor of the present invention is intended to be in continuous use twenty-four hours a day during all periods—which periods may be protracted and many months in duration—when the dilatation (or, equivalently, the effacement) of the cervix of the female patient wearing the monitor is of medical interest, it is possible for the monitor to make a visual or audible alarm when certain conditions are detected. Certain basic conditions regarding the cervical dilatation/effacement curing the onset of, and during the progress of, labor are well understood, and the monitor looks for, and alarms, the occurrence of these conditions.

It may well be, and is expected, however, that certain high-risk pregnancies will exhibit detectable, possibly unique, phenomena prior to events such as spontaneous abortion. If particular warning signs to the continuation of the pregnancy of a particular human female, or class of human females, can be recognized from the study of historical data on such female, or on such class of females, then it is contemplated that it will be desirable to warn such a female or females of the incipient occurrences of such signs in her/their later pregnancies. As will be seen, the ambulatory cervical monitor of the present invention is a programmable device. If necessary of desired, it can be preset to alarm, and to variously alarm, conditional upon almost any condition(s) of the cervix transpiring over almost any time interval(s) that the monitor is capable of detecting.

Although setting up the ambulatory cervical monitor of the present invention to alarm upon arbitrarily determined criteria (one, or many) involves (as of the present degree of understanding of cervical dilatation/effacement indications in high-risk pregnancies) highly skilled labor and attendant expense, it should be understood that the monitor is intended to be used, among other applications, on pregnant females that have never successfully carried so long so as to give live birth, let alone to term. Moreover, it should be understood that if cautions performed by the female and/or her medical advisors in response to monitor alarms and/or recorded records can prevent, or can even slightly delay by a matter of months or even scant weeks, highly premature births, then the very considerable expense of administering to premature newborns can be ameliorated, or even substantially saved.

This simple concept deserves further exposition. People do not like to, and effectively cannot, be told that they cannot have children because they are at risk of giving birth prematurely, and at great expense. People, especially those who desire but do not yet have children, do not like to think that such medical care, no matter how expensive, as might permit their prematurely born child to survive is being withheld on economic grounds. An ounce of prevention is worth a pound of cure—although it is perhaps not so "showy" in terms of hospital obstetrics facility, practice, and practitioners. A successful obstetrician in the current U.S. health care environment (circa 1994) is one who judiciously avoids problems, not just one who is skilled in overcoming problems. The monitor of the present invention is directed to aiding an obstetrician, a general health care practitioner, and a woman patient herself, in avoiding the expense, risk, and potentially traumatic consequences of premature birth.

A diagrammatic perspective view of a preferred embodiment of an ambulatory cervical effacement/dilatation monitor 1 having disposable probes 13 in accordance with the present invention in use for monitoring a pregnant human female 2 (shown partially in cut-away view and partially in phantom line) is shown in FIG. 2. The female 2 is ambulatory. Wires 12 connect a portable control unit 11 to the probes 13, The wires 12 descend (in the standing female) from the cervix os 21 whereat the probes 13 are affixed through the vagina (not shown)to the exterior of the body of the female 2. They then proceed past normal boundaries and apertures of both underclothing and clothing to the site of the control unit 11, which may be worn virtually anywhere on the body in a position covered or uncovered by clothing as is desired. The wires 12 are normally quite small and flexible, and are appropriately sheathed in soft and flexible plastic. The preferred surrounding plastic is preferably (i) surgical grade, (ii) antibacterial, (iii) and readily cleansed. The entire interconnection system of the wires 12 is designed with due consideration to (i) comfort for long term wear, and (ii) avoidance of establishing any path by which germs might abnormally be conducted to the region of surface of the cervix 21.

A detail diagram of the affixation of the disposable probes 13 of the ambulatory cervical effacement/dilatation monitor 1 in accordance with the present invention to the cervix uteri 21 of the pregnant human female 2 (previously seen in FIG. 1) is shown in FIG. 3. The particular affixation of the probes 13 that is illustrated is where each of the two probes is on the rim of the cervix 21 at roughly 180° separation. In this position the probes 13 are positioned to measure, by the delay in an ultrasound pulse traveling between them, the cervical dilatation, or distance across the cervix. Note that in the FIG. 3 it appears as if the central opening of the cervix os is void and filled with air, which would be unsuitable to transmit ultrasound. In actual fact the complete path in a substantially straight line between probes 13 is completely filled with tissues, mucous and fluids. It is not experienced that an ultrasonic path cannot be reliably established and maintained between the probes 13 under all normal and abnormal conditions. Indeed, neither ultrasonic signal attenuation nor change in attenuation (signal level) presents any significant problem(s) or challenge(s)—at least when the preferred probes are used (as will be discussed in conjunction with FIG. 4)—and there is little difficulty that (i) and ultrasonic pulse emitted at a one of the probes 13 will be duly received and the other one of the probes 13, and that (ii) this pulse will travel a true path, meaning straight between the two probes 13.

Figure 3B:
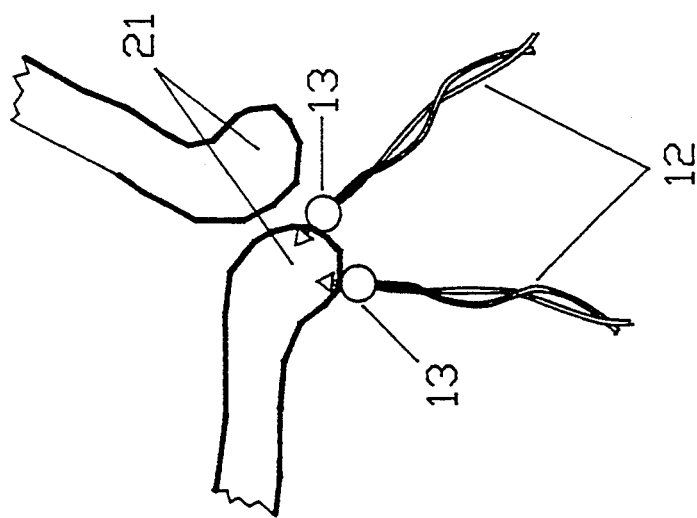
FIG. 3b is diagram, at an enlarged scale from FIG. 3b, of a second positions of affixation of the disposable probes to the cervix uteri of the pregnant human female previously seen in FIG. 2, the second affixation positions being so as to monitor cervical effacement.
Figure 3A:
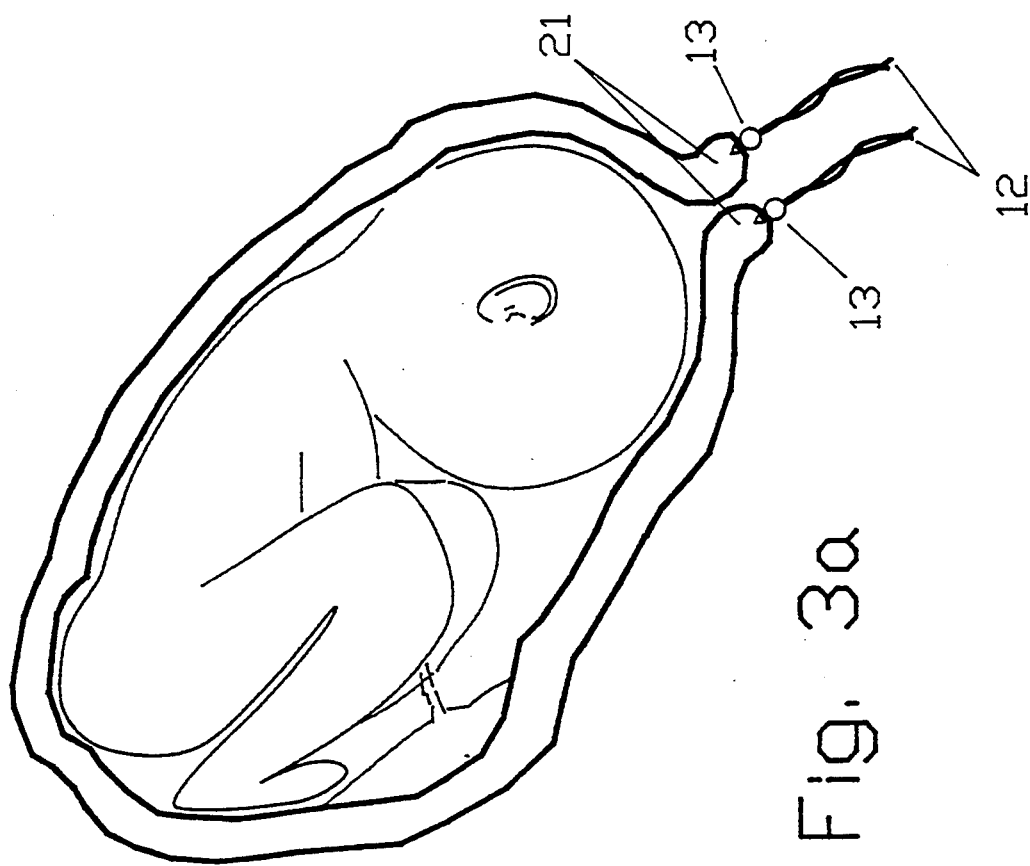
FIG. 3a is a detail diagram of first positions of affixation of the disposable probes of the ambulatory cervical effacement/dilatation monitor in accordance with the present invention to the cervix uteri of the ambulatory pregnant human female previously seen in FIG. 2, the first affixation positions being so as to monitor cervical dilatation.

A diagram, at an enlarged scale from FIG. 3b, of the affixation of the disposable probes to the cervix uteri of the pregnant human female in positions to monitor effacement is shown in FIG. 3b. The probes 13 are mounted along a same wall region, and normally on opposite sides of the wall, of the cervix os 21. When the cervix os 21 dilates (enlarges) then the distance between the probes 13 as such are attached in FIG. 3a will increase. However, during the same dilatation (enlargement) the distance between the probes 13 as such are attached in FIG. 3b will decrease. The increase is related (although not linearly) to the decrease, and vice versa. The status of the cervix os may be monitored, and interpreted, from data concerning either dilatation or effacement (or both). The normally measured, observed, monitored and interpreted quantity is dilatation, and the ensuing discussion of the function of the cervical monitor of the present invention will be based on dilatation. However, a practitioner of the medical arts will understand that these and other physiological measurements are interrelated, and that the monitoring and alarming function of the present invention is not dependent upon the particular placement of the probes 13, nor the particular path and distance that is monitored.

Figure 4C:
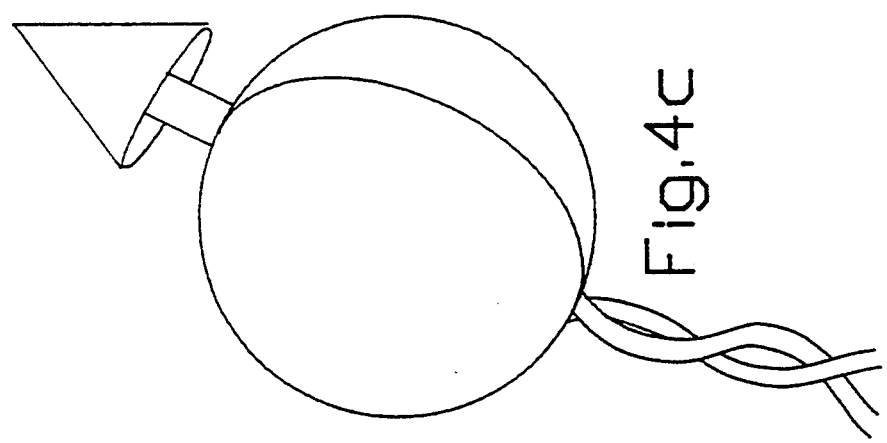
FIG. 4, consisting of FIG. 4a through FIG. 4c, show various preferred embodiments of the head of a disposable probes, two of which probes which are used with the preferred embodiment of the ambulatory cervical effacement/dilatation monitor in accordance with the present invention previously seen in FIGS. 2 and 3.
Figure 4B:
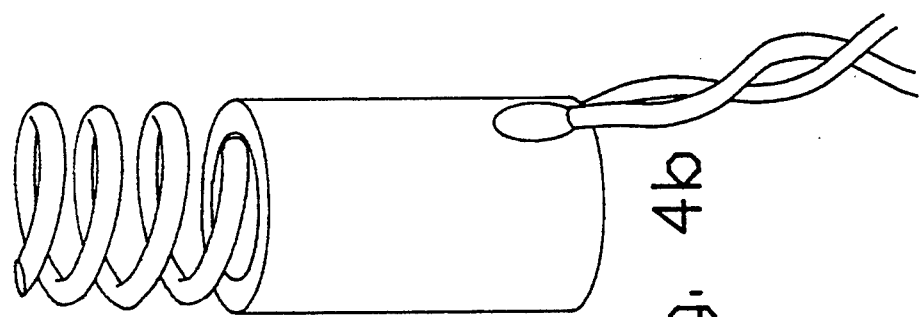
Figure 4A:
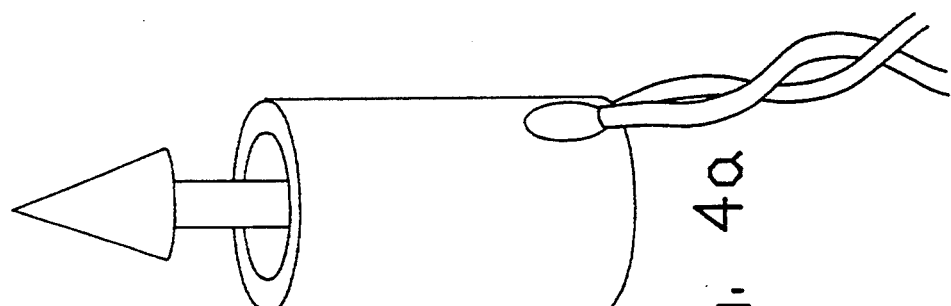

Various preferred embodiments of the head of a disposable probes, two of probes which are used with the preferred embodiment of the ambulatory cervical effacement/dilatation monitor in accordance with the present invention previously seen in FIGS. 2 and 3, are shown in FIG. 4, consisting of FIG. 4a through FIG. 4c. The body of the embodiments of FIGS. 4a and 4b is substantially cylindrical whereas the embodiment of FIGS. 4c is substantially spherical. The transducer of each of these two body configurations is in the substantial shapes of a three-dimensional, non-planar, bodies. This is somewhat unusual because an ultrasonic transducer is normally housed in a substantially planar parallelepiped body, typically a disk. Such need not be the case, however. The ultrasound, which is electrically produced in a crystal, will radiate from the surface of the surrounding housing, whatsoever its shape.

Each of the preferred transducer bodies shown in FIGS. 4a–4c is characterized in that ultrasound emissions from the transducer occur along a multiplicity of axis in multiple different directions. The reason that the transducers are so omnidirectional is that, when secured to the wall of the cervix uteri of human female such as by their barbed fishhook or corkscrew coil (to be discussed), the transducers are substantially insensitive to their initial placement(s) and alignment(s), and also to any directional changes occurring before or during labor. The preferred transducers serve to maintain good acoustic coupling under all conditions.

It is, or course, necessary to maintain the transducers 13 in their predetermined, fixed, locations upon the cervix os 21 so that ultrasonic transit time measurements may be performed. There are insubstantial nerve endings on the cervix os, which is also physically very robust and resilient to permanent damage. Ultrasonic probes have heretofore been attached by corkscrews, and that embodiment of a probe 13 in accordance with the present invention that is shown in FIG. 4b continues this tradition. Corkscrews are a good, and proven, means of attachment of probes to muscle, as witness cardiac pacemakers. However, there are differences between cardiac probes and ultrasonic transducers. In the former case an electrical signal is being coupled to the muscle, and reliable continuous electrical and physical contact must be maintained therewith. In the present ultrasonic probes, understand that no electrical, nor acoustical, energy is being attempted to be coupled into the muscle (of the cervix os) through, or by, the probe attachment. There is, or course, no electrical coupling to the muscle. The acoustic coupling is, by and large, to the surrounding mucous and fluids, and the probe is not configured for coupling acoustic energy into the cervix os (if it was then should lie tight against the cervix ios). The probes'attachments are simply to hold the probes in position so that they may follow the movement of the muscle, and so that the varying distance between them may be monitored.

So considering the function of the attachment of a probe 13, the barbs of the embodiments of FIGS. 4a and 4c, of like barbs in the substantial shapes of fishhooks, are preferred for some patients. Namely, the barbed probes are generally easier, and faster, to attach in patients who are sensitive to discomfort. A corkscrew probe should be unscrewed in order to remove, but a barbed probe of the design of FIGS. 4a and 4c will usually exit cleanly if simply pulled strongly. In those generally rare affixations, and locations, where a fishhook barb (not shown) better serves retention, and positioning of the probe, then the barb may be removed exactly as a fishhook is removed from the flesh of the body. Namely, the barb is worked forward to exit the surface, and is cut off as exposed. The barb-less probe is then withdrawn.

Figure 5A:
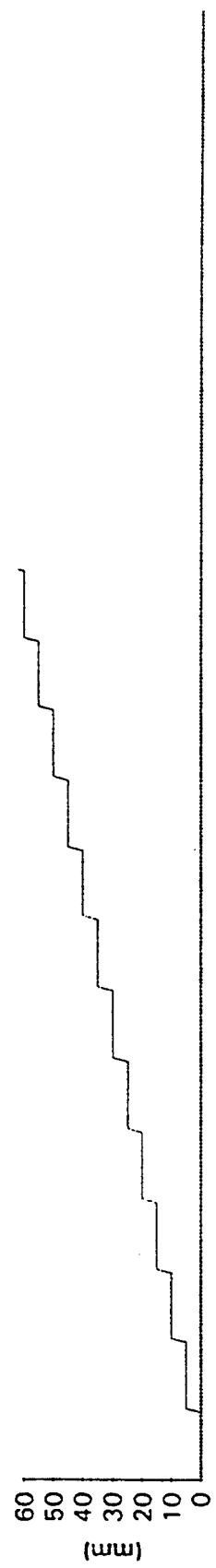
FIG. 5a is a graph showing a calibration of the ambulatory cervical effacement/dilatation monitor in accordance with the present invention.

A graph showing a calibration of the ambulatory cervical effacement/dilatation monitor in accordance with the present invention is shown in FIG. 5a. The calibration is performed in the controller 11 by producing in manually controllable steps successive delays such as would be indicative, if received from probes 13, of an increasing amount of separation between the probes 13. The "manually controllable steps" simply involve the stepwise rotation of a multiple position switch which, in its successive positions, couples an increasing amount of delay into the simulated probe input to the controller 11 (the schematic diagram of which controller 11 will be shown in FIGS. 6 and 7). The lowest level of the trace in the graph of FIG. 5a is indicative of a probe separation of 10 mm; the highest level of the trace is indicative of a probe separation of 60 mm. If the number of steps are carefully counted, if may be observed that the preferred resolution of the cervimeter monitor 1 is at least as small as 5 mm.

Figure 5B:
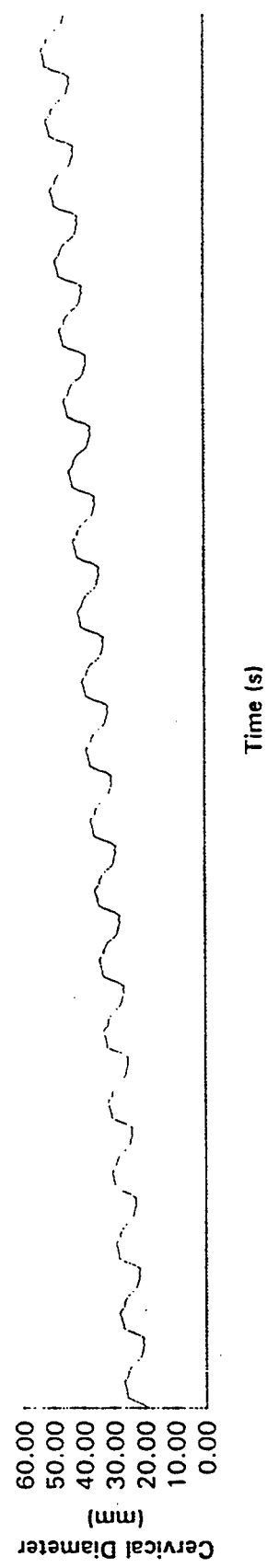
FIG. 5b is a graph showing the typically varying dilatation of the cervix uteri of a human female, or any higher primate, during labor.

FIG. 5b is a graph showing the typical varying dilatation of the cervix uteri of a human female, or other higher primate such as a rhesus monkey, during labor. The total period shown is about thirty (30) minutes in which period twenty (20) relatively even cycles have transpired for an average cycle time of one and one-half ($1\frac{1}{2}$) minutes per cycle.

A schematic block diagram of a substantially analog first portion 11 of the preferred embodiment of the ambulatory cervical effacement/dilatation monitor 1 in accordance with the present invention is shown in FIG. 6. The first portion 11 is, in of itself, a complete sonomicrometer. Sonomicrometers are known in the art, and the circuit of the block diagram of FIG. 6 is simply a particular version of a sonomicrometer that is, quite obviously, adapted to the measurement task at hand in terms of (i) acoustic signal power, (ii) acoustic signal reception sensitivity, and, most importantly, (iii) the duration (not the frequency) of an acoustic signal pulse that will be appropriate to measure the distances involved in cervical dilatation, and (iv) a repetition rate of the acoustic signal pulse that will be appropriate to measure all changes in the distances involved in cervical dilatation. Notably, the frequency of the acoustic signal is an innate property of the probes, or transducers 13, which "ring" when electrically excited at their resonant frequency(ies). The probes, or transducers, 13 may suitably operate over a broad range of ultrasonic frequencies, and preferably ring at a natural resonant frequency of about 5 Mhz.

A CLOCK portion of the CLOCK AND TIMING 111 produces a fundamental 1.58 MHz frequency. This frequency is chosen because an ultrasonic acoustic pulse will travel approximately 1 millimeter in tissue—and very nearly the same in mucous or other water-based fluids—in the period of one cycle of 1.58 MHz, or 0.63 microseconds. The 1.58 Mhz signal is provided as signal CLOCK 111.

A TIMING portion of the CLOCK AND TIMING 112 produces pulses of (i) 50 microsecond duration (of 1.58 MHz signal) (ii) at a pulse repetition rate of 100 Hz. The duty cycle of the collective pulses is correspondingly (($5 \times 10^{-5}) \times 1 \times 10^2$) per second, or a low 0.5% which serves to save power. These 50 microsecond pulses at the 100 Hz. rate are applied to the set, or S, input of the PULSE GENERATOR 116 and the PINGER 114. The PINGER 116 serves as an amplifier. The 50 microsecond pulse duration is sufficient, when driven by the PINGER 114, so as to cause the driven one of the probes, or transducers, 13 to ring, producing an acoustic pulse (which gradually decays in amplitude) for an effective duration, as is such pulse is detectable at the other one of the transducers 13 and by the RECEIVER 118, of about 1 msec. (One hundred such acoustic pulses each second give an acoustic duty cycle of approximately 10%.) The duration of this acoustic pulse is, or course, not particularly important save that each pulse shall have completely died away before a next later pulse is generated. In accordance with the principles of transit time sonomicrometry, it is the delay incurred by this pulse in reaching the receiving one of the probes, or transducers 13 that is important. Each and every pulse will incur a delay of about 0.63 microseconds per millimeter traversed.

The signal developed in the RECEIVER 118 in response to each received acoustic pulse is shaped in an automatic gain control, AGC, circuit 120 and is then subject to detection in LEVEL DETECT circuit 122. The signal AGC VOLTAGE 113 is a function of the amount of signal gain being applied in, and by, the AGC circuit 120, and will be highest when the received signal acoustic is lowest, or non-existent (as between acoustic pulses, or before an acoustic pulse has arrived). A use of such signal AGC VOLTAGE 113 will be later shown in FIG. 7. The signal output of LEVEL DETECT circuit 122 will assume a logic High condition within a few tens of nanoseconds that the acoustic pulse is received by the RECEIVER 118. The signal will, as applied to the reset, or R, input of the PULSE GENerator circuit 114, serve to reset this circuit. (It will be understood that electrical delays are small in relation to acoustic delays in a sonomicrometer.) The signal PULSE 115 arising from the PULSE GENerator circuit 114 accordingly starts with each transmission of an acoustic pulse, and ends with the reception of the same pulse. Its duration is thus indicative of the acoustic delay in the communication of the ultrasonic pulse between the two transducers 13.

Figure 7:
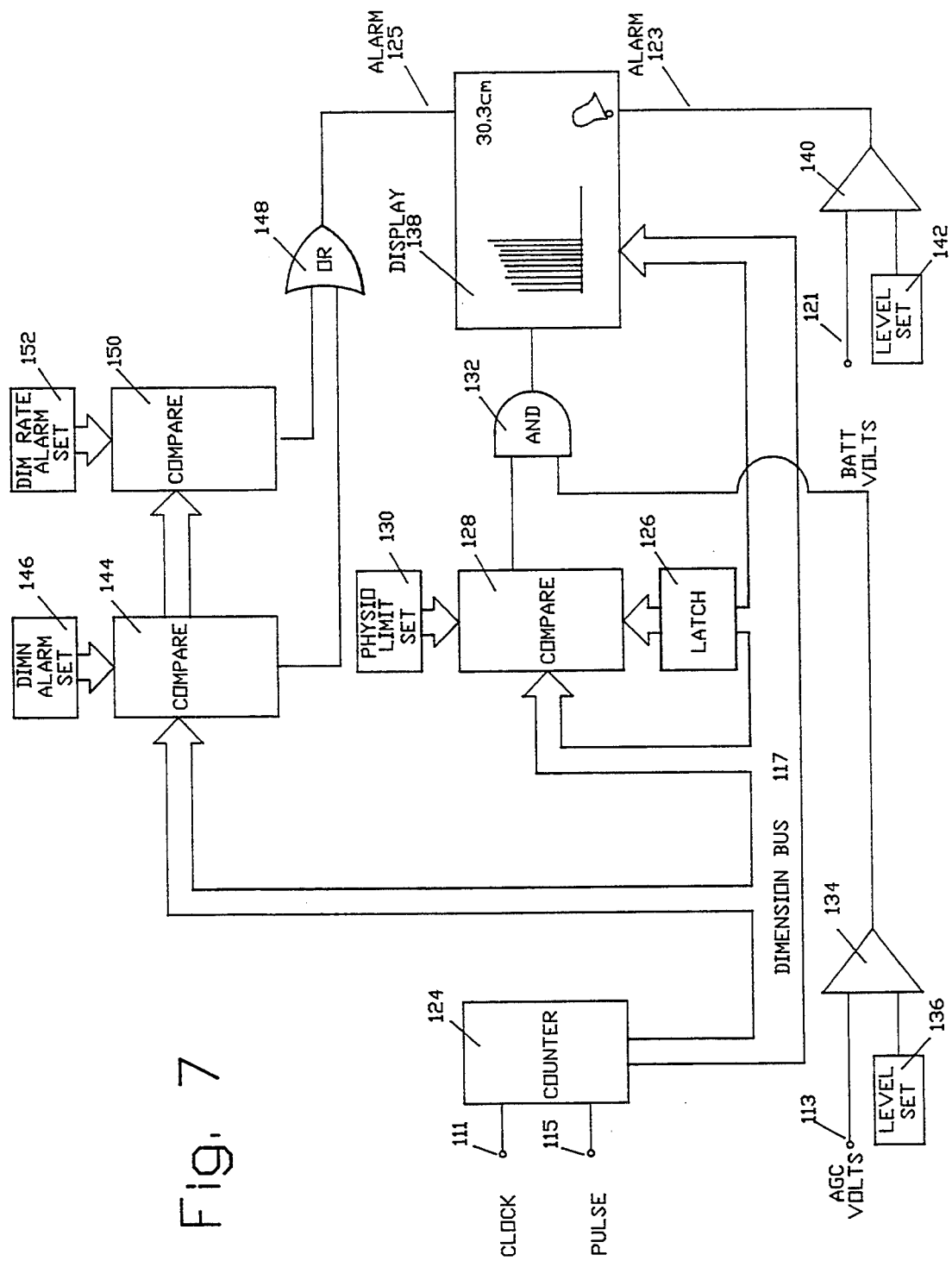
FIG. 7 is a schematic block diagram of a substantially digital second portion of the preferred embodiment of the ambulatory cervical effacement/dilatation monitor in accordance with the present invention, the analog portion of which ambulatory cervical effacement/dilatation monitor was previously seen in FIG. 6.

FIG. 7 is a schematic block diagram of a substantially digital second, data logger and alarming, portion of the preferred embodiment of the ambulatory cervical effacement/dilatation monitor 1 in accordance with the present invention. This data logger and alarming portion receives all three signals 111, 113, and 115 developed in the analog, sonomicrometer, portion previously seen in FIG. 6. The signal CLOCK, which is at a frequency of 1.58 Mhz, serves to increment a COUNTER 124 that is enabled for counting for the duration of signal PULSE 115. The number of counts accrued during the duration of each signal PULSE 115 is the thus the distance in millimeters that the ultrasonic acoustic signal traversed between probes 13 (shown in FIG. 6). Permitting the COUNTER 124 to read directly in millimeters avoids the necessity of a later conversion. Once the count is terminated by the logic Low condition of signal PULSE 115, the COUNTER 124 will put the accrued count onto a digital communications bus that is called DIMENSION BUS 117 because it carries the cervical dimension. The COUNTER 124 will also reset itself to zero for the next counting interval (which, in accordance with CLOCK AND TIMING 112 shown in FIG. 6, will occur in 10 milliseconds).

The current count, which is the cervical dilatation (or effacement) in millimeters is received into a LATCH 126 and a COMPARE circuit 128. The COMPARE circuit 128 also receives a digital quantity from the PHYSIO LIMIT SET register 130. This quantity represents the greatest reasonable, real-world, change that would be expected in cervical dilatation over the time interval between successive counts, or 10 milliseconds. This quantity is equivalent to a change in cervical diameter of about 1 millimeter per second. The previous cervical measurement that stored in LATCH 126 is compared with the current cervical measurement received via DIMENSION BUS 117, and with the maximum expected change received from PHYSIO LIMIT SET register 130 in order to make the single determination that the presently-received cervical dimension either is, or is not, reasonable. An unreasonable reading might be received, for example, due to ultrasonic noise.

If the cervical dimension, as is upon the DIMENSION BUS 117, is reasonable then the input from the COMPARE circuit 128 to the AND gate 132 is a logic High, satisfying one of the two inputs to AND gate 132.

The other, remaining, input to the AND gate 132 is derived from differential amplifier 134. The signal 119 from this differential amplifier 134 will be a logic High, satisfying the remaining one of the inputs to AND gate 132, at such times as the signal AGC VOLTAGE 113 is greater than a preset signal level supplied from the reference voltage level, or LEVEL SET 136. The signal AGC VOLTAGE 113 will so be greater than the preset signal level supplied from reference voltage level SET 136 when, and upon such times, as the RECEIVER 118 (shown in FIG. 6) is not receiving an ultrasonic pulse. According to being in an interval between the reception of ultrasound, the COUNTER 124 is not incrementing, and the cervical dimension that is upon the DIMENSION BUS 117 driven from the COUNTER 124 is (momentarily) stable, and invariant. Satisfaction of the AND gate 132 will produce a logic High gating signal to the DISPLAY 138, and will cause the DISPLAY 138 to capture the cervical dimension quantity that is upon the DIMENSION BUS 117 and to display it as a vertical bar in a next successive position proceeding towards the right across a visual display area.

The display 138, if not substantially the entire data logger shown in FIG. 7, may optionally, and even preferably, based upon a microprocessor. A practitioner of the digital logic design arts will have no difficulty in accomplishing the counting and comparison functions already discussed in FIG. 7, as well as certain other functions to be discussed, in the logic and the registers of a microprogrammed microprocessor. A microprocessor may, for example, scale the cervical dimension received on DIMENSION BUS 117 in order to appropriately size, and place, a graphical display on the DISPLAY 138. Indeed, almost as soon as the practitioner of the digital logic design arts starts to think about the flexibility, and power, of a microprocessor as applied to the data logging and alarming task of FIG. 7, it is possible to realize that, other than the necessity of comparing analog signal levels in the differential amplifier 134 (and also in differential amplifier 140, yet to be discussed) and displaying data in the DISPLAY 138, veritably everything could be done in a microprocessor. In such a case FIG. 7 could be equally validly considered as a functional, as opposed to a hardware, block diagram.

The preferred implementation of the present invention is, as is shown in FIG. 7, to (i) use a microprocessor (not shown) as part of DISPLAY 138, but (ii) not to place have all such functionality as might conceivably be accomplished by the microprocessor so accomplished. This is for two reasons not immediately apparent on the face of FIG. 7. First, it is contemplate that, with an appropriate data storage memory and sequential memory addressing (not shown) that a power-consuming microprocessor and a visual display might be turned off for periods of time and from time to time, saving energy when no one cares to view historical cervical dilatation (effacement) data in the DISPLAY 138. Second, and although various alarms the development of which is yet to be discussed are shown to be communicated directly to the DISPLAY 138, and presumably to any microprocessor (not shown) lodged therein, if is very simple to understand that, by use of discrete circuits no more complex than a latch, it would be possible to register, and to sound and/or display (in the form of a light, or LED), one or more alarms without the involvement of any microprocessor, or microcode program. Although outside the scope of the present disclosure, the data logging and alarming circuitry of FIG. 7 can thus readily be made to have (i) a reduced-power, fullback, operational mode, and/or (ii) substantially fail-safe operation.

An alarming monitor of cervical dilatation/effacement does not incur the reliability requirements of, for example, a cardiac pacemaker. If the instrument fails the patient neither aborts, nor gives birth, nor suffers any adverse effects whatsoever. However, it is anticipated that, in some pregnancies, successful live birth may be dependent upon the adequacy and continuity of the cervical monitoring, and the timely administration of all such interventions (primarily drugs) as are indicated to be prudent and necessary as a result of such monitoring. Accordingly, the cervical dilatation (or effacement) monitor is desirably, and is, constructed as a quality instrument, with due regard by design for it potentially crucial function.

Continuing in FIG. 7, a battery (not shown), nominally of a 9 v.d.c. type which typically suffices to last at least two (2) weeks and more commonly two (2) months in continuous use, produces a battery voltage BATT VOLTS 121. This battery voltage is compared in differential amplifier 140 to the voltage output of a constant voltage circuit LEVEL SET 142. Until, an unless, the battery voltage falls below a predetermined level, normally eight (8) v.d.c., the signal ALARM 123 will be maintained a logic High level, and the DISPLAY 138 will not produce an alarm. At any such times as the battery voltage were to fall below the predetermined level the signal ALARM 123 will go to a Logic Low level, and the DISPLAY 138 will produce a visual and/or audible alarm in plenty of time to replace the battery (not shown) before power reserves are exhausted.

A comparison of the cervical dilatation (effacement) measurement as is present on the DIMENSION BUS 117 is made in, and by, COMPARE circuit 144 to a predetermined dimension that is stored in the DIMN ALARM SET register 146. The DIMN ALARM SET register 146 is intended to contain a maximum dimension in the case of evaluating cervical dilatation, or, conversely, a minimum dimension in the case of evaluating cervical effacement, which, when the cervical dimension is respectively greater than or less than the stored dimension, is indicative that labor has begun (or at least of an extreme cervical condition). The result of the comparison is communicated to OR gate 148 as a logic High signal in the event that the threshold is exceeded. The predetermined dimension that is stored in the DIMN ALARM SET register 146 is preferably adjustably so predetermined, and stored. A microprocessor (not shown, typically closely associated with DISPLAY 138) may facilitate this storage, normally of a value that is determined by the attending physician or obstetrician.

In a similar manner, another comparison of the cervical dilatation (effacement) measurement made in, and by, COMPARE circuit 152 to a predetermined dimension that is stored in the DIMN PATE ALARM SET register 152. Notably, the cervical dimension is not even transferred to the COMPARE circuit 152 until the COMPARE circuit 144 is satisfied, meaning that a threshold cervical dilatation/effacement measurement has been exceeded. The DIMN RATE ALARM SET register 152 is intended to contain a minimum rate of the change of dimension cervical dilatation, or effacement. This quantity is involved once labor has begun (which was presumptively determined by satisfaction of COMPARE Circuit 144). If the predetermined rate of change is not exceeded then this may be indicative of problems with the progress of labor. The result of the comparison is also communicated to OR gate 148 as a logic High signal in the event that the predetermined rate of change is not exceeded. The predetermined rate of change that is stored in the DIMN RATE ALARM SET register 152 is preferably adjustably so predetermined, and stored. A microprocessor (not shown, typically closely associated with DISPLAY 138) again facilitates this storage, normally again of a value that is determined by the attending physician or obstetrician.

Satisfaction of the OR gate 148 produces a logic High signal ALARM 125, which signals received into DISPLAY 125 is used to produce a visual and/or audio alarm.

Figure 8:
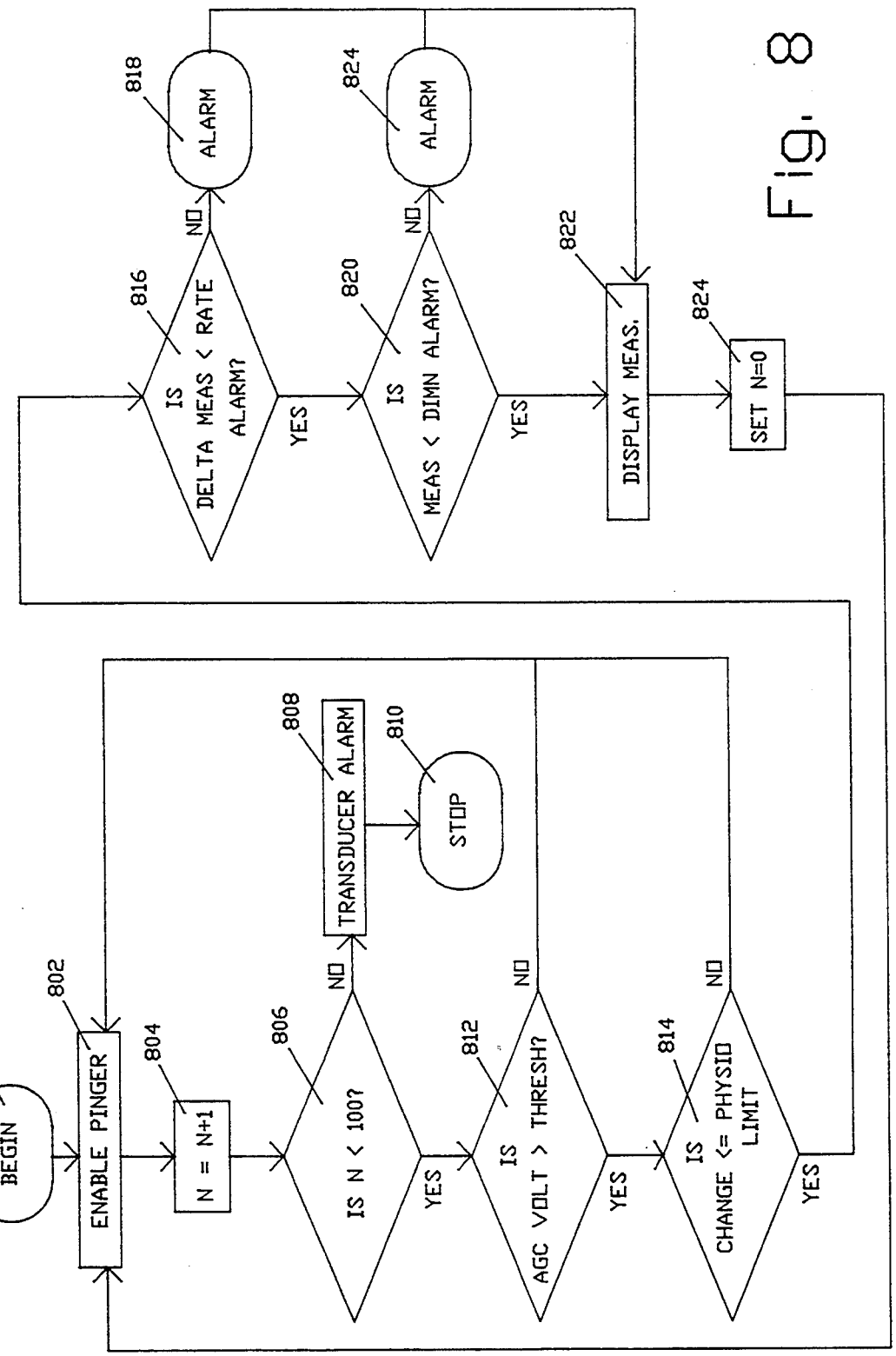
FIG. 8 is a flow chart of the function of the preferred embodiment of the ambulatory cervical effacement/dilatation monitor in accordance with the present invention previously seen in perspective view in FIG. 2, and in schematic block diagram in FIGS. 6 and 7.

A flow chart of the function of the preferred embodiment of the ambulatory cervical effacement/dilatation monitor 1 in accordance with the present invention is shown in FIG. 8. The flow chart is, as well as being functional, suitable to serve as the flow chart of a sequential controller, particularly (but not necessarily) including a microprogrammed microprocessor. It will be recognized by a practitioner of the digital circuit design arts that the relative simplicity of the functional control block diagrammed in FIG. 8 may be accomplished by, and in, many alternative circuit implementations including, but not limited to, a microprogrammed microprocessor circuit.

The function of the ambulatory cervical effacement/dilatation monitor 1 commences with BEGIN block 800 upon application of power, and proceeds to commencing ultrasound transmission with ENABLE PINGER block 802. An ultrasound, or "ping", transmission count N is incremented in block 804, and inquiry is made as to whether this count has exceeded 100 in block 806. As will be developed in the further explanation of FIG. 8, it is a highly abnormal condition, indicating that at least 101 ultrasound pulses have been transmitted with no intervening receptions, if N is greater than 100. In such an eventuality, transducer or transducer interconnect hardware failure is indicated, and a TRANSDUCER ALARM is sounded in block 808 and the monitor 1 brought to a STOP in block 810.

Normally block 806 is satisfied, and the inquiry as to whether the Automatic Gain Control (AGC) voltage is greater than a threshold—AGC VOLT >THRESHOLD—is made in block 812. If not, no ultrasonic pulse has as yet been received, and the transmission process is re-enabled commencing with block 802.

If a received pulse is detected in block 812, then a reasonability check on the detected delay is performed in block 814. It is therein inquired as to whether the detected change is within the physiological limits of the human subject, IS CHANGE←PHYSIO LIMIT? In the event that it is not, process error has occurred and the transmission process is again re-enabled commencing with block 802.

If, however, all status and reasonableness checks of blocks 806, 812 and 814 are satisfied, block 816 is entered to assess whether the change in measurements dictates a rate alarm. If the measurement change does not exceed the predetermined alarm threshold, then DELTA MEAS <RATE ALARM? is answered yes and block 820 is entered. Should, however, the measurement change exceed the predetermined alarm threshold, then an ALARM is indicated in block 818.

Similarly, block 820 is entered to assess whether the absolute magnitude of the measurement dictates an alarm. If the measurement change does not exceed a predetermined alarm threshold dimension, then MEAS <DIMN ALARM? is answered yes and block 822 is entered. Should, however, the measured dimension exceed the predetermined alarm threshold dimension, then an ALARM is indicated in block 824.

Whether a dimension, or a dimensional change, has occasioned the respective ALARM of block 824, of or block 818, or not, the block 822 DISPLAY MEAS is always entered and the measurement displayed. The count number of the ultrasound transmission is thereafter reset to zero—SET N=0—in block 824, and the entire loop process re-entered at block 802.

In accordance with the preceding explanation, many variations and alterations of the preferred embodiment of the present invention will suggest themselves to a practitioner of the electronic medical equipment design arts. For example, many more separate, and detailed, alarms could be made contingent upon conditions which may be quite intricate, and convolute. For example, the display, and history display, could be of alternative intervals and epochs.

In accordance with these and other possible variations and adaptations of the present invention, the scope of the invention should be determined in accordance with the following claims, only, and not solely in accordance with that embodiment within which the invention has been taught.

What is claimed is:

1. A probe for use with an ultrasonic transit time cervimeter, the probe comprising:
   a transducer in the substantial shape of a three-dimensional, non-planar, body characterized in that ultrasound emissions from the transducer are along a multiplicity of axis in multiple different directions;
   means for securing the transducer to the wall of the cervix uteri of human female; and
   an electrical wire adapted for connecting between the transducer in its position secured to the wall of the cervix and an ultrasonic transit time cervimeter in a location exterior to human female's body.

2. The probe according to claim 1 wherein the transducer is in the substantial shape of a cylinder characterized in that ultrasound emissions from the cylindrically-shaped transducer assembly are along a multiplicity of axis in multiple directions all substantially perpendicular to an imaginary central axis of the cylinder.

3. The probe according to claim 1 wherein the transducer is in the substantial shape of a sphere characterized in that ultrasound emissions from the spherically-shaped transducer assembly are along a multiplicity of axis in multiple directions all substantially radial to an imaginary centroid of the sphere.

4. The probe according to claim 1 wherein the securing means comprises:
   a barbed hook engaging the wall of the cervix uteri of the human female when stuck therein.

5. The probe according to claim 1 wherein the securing means comprises:

a corkscrew coil engaging the wall of the cervix uteri of the human female when threaded therein.

6. An ultrasonic transit time cervimeter comprising:
an ultrasonic transmitter in the substantial shape of a three-dimensional, non-planar, body characterized in that ultrasound is emitted from the transmitter along a multiplicity of axis in multiple different directions;
an ultrasonic receiver in the substantial shape of a three-dimensional, non-planar, body characterized in that ultrasound is received along a multiplicity of axis from multiple different directions;
a means for securing the ultrasonic transmitter, and also the ultrasonic receiver, to the wall of the cervix uteri of human female at spaced apart positions so that a straight line ultrasonic acoustic path at least partially through the cervix exists between the ultrasonic transmitter and the ultrasonic receiver, the path being simultaneously along at least one ultrasound emission axis of the ultrasonic transmitter and at least one ultrasound reception axis of the ultrasonic receiver;
an ultrasonic transit time micrometer for detecting a delay in the propagation of ultrasound from the ultrasonic transmitter to the ultrasonic receiver as an indication of the dilatation of the cervix uteri; and
electrical wires adapted for connecting both the ultrasonic transmitter and the ultrasonic receiver in their positions secured to the wall of the cervix to the ultrasonic transit time micrometer.

7. The ultrasonic transit time cervimeter according to claim 6 wherein at least one of the ultrasonic transmitter and the ultrasonic receiver comprises:
an ultrasonic transducer in the substantial shape of a cylinder.

8. The ultrasonic transit time cervimeter according to claim 6 wherein at least one of the ultrasonic transmitter and the ultrasonic receiver comprises:
an ultrasonic transducer in the substantial shape of a sphere.

9. The ultrasonic transit time cervimeter according to claim 6 wherein the securing means comprises:
a barbed hook engaging the wall of the cervix uteri of the human female when stuck therein.

10. The ultrasonic transit time cervimeter according to claim 6 wherein the securing means comprises:
a corkscrew coil engaging the wall of the cervix uteri of the human female when threaded therein.

11. The ultrasonic transit time cervimeter according to claim 6 wherein the ultrasonic transit time micrometer comprises:
a first alarm circuit for causing an alarm upon such times as the detected ultrasound delay varies sufficiently regularly over time so as to, by indicating a corresponding temporally regular variation in the dilatation of the cervix uteri, mark the onset of labor.

12. The ultrasonic transit time cervimeter according to claim 11 wherein the ultrasonic transit time micrometer comprises:
another, second, alarm, circuit enabled only after actuation of the first alarm and upon such times as the detected ultrasound delay exhibits an insufficient variation over time so as to, by indicating a lack of temporal variation in the dilatation of the cervix uteri, mark the onset of problems with labor.

13. The ultrasonic transit time cervimeter according to claim 6 wherein the ultrasonic transit time micrometer comprises:
an alarm upon circuit for causing an alarm upon, such times as the detected ultrasound delay is sufficiently great so as to indicate that the dilatation of the cervix uteri has exceeded a predetermined size.

14. An ultrasonic transit time cervical dilatation monitor comprising:
an ultrasonic transmitter;
an ultrasonic receiver;
a means for securing the ultrasonic transmitter, and also the ultrasonic receiver, to the wall of the cervix uteri of human female at spaced apart positions so that an ultrasonic acoustic path at least partially through the cervix exists between the ultrasonic transmitter and the ultrasonic receiver;
an ultrasonic transit time micrometer, connected to both the ultrasonic transmitter and the ultrasonic receiver in their positions secured to the wall of the cervix, for detecting a delay in the propagation of ultrasound from the ultrasonic transmitter to the ultrasonic receiver as an indication of the dilatation of the cervix uteri;
a monitor for monitoring dilatation of the cervix uteri and for causing an alarm if a predetermined condition of dilatation is detected.

15. The ultrasonic transit time cervical dilatation monitor according to claim 14 wherein the monitor of the indicated dilatation of the cervix uteri is causing the alarm upon the monitoring of regular temporal variations in the dilatation of the cervix, indicating the onset of labor.

16. The ultrasonic transit time cervical dilatation monitor according to claim 14 wherein the monitor of the indicated dilatation of the cervix uteri is causing the alarm upon a cessation of any temporal variations in the dilatation of the cervix, indicating an onset of problems once labor has commenced.

17. The ultrasonic transit time cervical dilatation monitor according to claim 14 wherein the monitor of the indicated dilatation of the cervix uteri is causing the alarm upon the dilatation of the cervix exceeding a predetermined distance.

18. An automated method of monitoring cervical dilatation comprising:
securing an ultrasonic transmitter and an ultrasonic receiver at spaced-apart positions upon the wall of the cervix uteri;
energizing the secured ultrasonic transmitter and ultrasonic receiver with and by an ultrasonic transit time micrometer;
detecting the ultrasound propagation transit time from the ultrasonic transmitter to the ultrasonic receiver with and by use of the ultrasonic transit time micrometer in order to provide an indication of the corresponding dilatation of the cervix uteri;
electronically monitoring the detected transit time, and the indicated dilatation of the cervix uteri corresponding to the detected transit time, in order so as to sound an alarm if a predetermined condition of dilatation is detected.

19. The automated method of monitoring cervical dilatation according to claim 18
wherein the electronically monitoring is of a detected transit time, and of a correspondingly indicated dilatation, that marks the onset of labor.

20. The automated method of monitoring cervical dilatation according to claim 18
   wherein the electronically monitoring is of detected delay, and of a correspondingly indicated dilatation, that marks, once labor has commenced, the onset of problems with labor.

21. The automated method of monitoring cervical dilatation according to claim 18
   wherein the electronically monitoring is of detected delay, and correspondingly indicated dilatation, so as mark that the dilatation of the cervix uteri has exceeded a predetermined distance.

22. The automated method of monitoring cervical dilatation according to claim 18
   wherein the securing of the ultrasonic transmitter and the ultrasonic receiver is at spaced-apart positions between a first point upon an interior wall of the cervix uteri and a second point, the second point radially disposed radially outwardly from the first point along an extension of an imaginary vector between an imaginary central axis of the cervix uteri and the first point; and
   wherein the detecting is of the delay in the propagation transit time of ultrasound from the first point to the second point along an imaginary radius of the cervix uteri.

23. The automated method of monitoring cervical dilatation according to claim 18
   wherein the securing of the ultrasonic transmitter and the ultrasonic receiver is at spaced-apart positions between two points located upon an imaginary arc segment of the wall of the cervix uteri; and
   wherein the detecting is of the delay in the propagation transit time of ultrasound between the two points along an imaginary arc segment of the cervix uteri.

24. A real-time ambulatory recording and displaying monitor of the cervix uteri comprising;
   an ultrasonic transmitter;
   an ultrasonic receiver;
   a means for securing the ultrasonic transmitter, and also the ultrasonic receiver, to the wall of the cervix uteri of human female at spaced apart positions so that a straight line ultrasonic acoustic path at least partially within the cervix exists between the ultrasonic transmitter and the ultrasonic receiver; and
   a case suitable for attachment to the body containing
      an ultrasonic transit time micrometer electrically connected to both the ultrasonic transmitter and the ultrasonic receiver in their positions secured to the wall of the cervix, for detecting a delay in the propagation of ultrasound from the ultrasonic transmitter to the ultrasonic receiver as an indication of the dilatation of the cervix uteri,
      a memory for storing the delays as are detected over time as an indication of the dilatation of the cervix uteri over time, and
      a display for displaying at times each of the present dilatation of the cervix uteri, and also the dilatation of the cervix uteri over time.

25. The real-time ambulatory recording and displaying monitor of the cervix uteri according to claim 24 further for alarming, the monitor further comprising within case suitable for attachment to the body:
   an alarm circuit for alarming if the indicated dilatation of the cervix uteri equals a predetermined condition.

26. The real-time ambulatory recording, displaying and alarming monitor of the cervix uteri according to claim 25
   wherein the alarm circuit is further for alarming if the indicated history of the dilatation of the cervix uteri equals a predetermined condition.

* * * * *